US009820920B2

(12) United States Patent
Nikitczuk et al.

(10) Patent No.: US 9,820,920 B2
(45) Date of Patent: Nov. 21, 2017

(54) HIGH UV PROTECTION ALCOHOL-FREE EMULSION SYSTEM, THAT IS CLEAR ON APPLICATION

(71) Applicant: L'OREAL, Paris (FR)

(72) Inventors: Kevin Nikitczuk, Skillman, NJ (US); Anil Shah, East Windsor, NJ (US); Susan Halpern Chirch, Basking Ridge, NJ (US); Jean-Thierry Simonnet, Ruel Mailmaison (FR)

(73) Assignee: L'Oreal, Paris (FR)

( * ) Notice: Subject to any disclaimer, the term of this patent is extended or adjusted under 35 U.S.C. 154(b) by 147 days.

(21) Appl. No.: 14/502,566

(22) Filed: Sep. 30, 2014

(65) Prior Publication Data

US 2016/0089311 A1 Mar. 31, 2016

(51) Int. Cl.
*A61K 8/06* (2006.01)
*A61K 8/49* (2006.01)
*A61K 8/44* (2006.01)
*A61K 8/02* (2006.01)
*A61K 47/00* (2006.01)
*A61K 47/30* (2006.01)
*A61Q 17/04* (2006.01)
*A61K 45/06* (2006.01)

(52) U.S. Cl.
CPC ............ *A61K 8/062* (2013.01); *A61K 8/0241* (2013.01); *A61K 8/44* (2013.01); *A61K 8/4993* (2013.01); *A61K 45/06* (2013.01); *A61Q 17/04* (2013.01); *A61K 2800/21* (2013.01); *A61K 2800/262* (2013.01); *A61K 2800/30* (2013.01)

(58) Field of Classification Search
None
See application file for complete search history.

(56) References Cited

U.S. PATENT DOCUMENTS

| 2,463,264 | A |   | 3/1949  | Graenacher et al. |             |
|-----------|---|---|---------|-------------------|-------------|
| 5,166,355 | A |   | 11/1992 | Leistner et al.   |             |
| 5,188,831 | A | * | 2/1993  | Nicoll            | A61Q 17/04  |
|           |   |   |         |                   | 424/401     |
| 5,237,071 | A |   | 8/1993  | Leistner et al.   |             |
| 5,585,091 | A |   | 12/1996 | Pelzer et al.     |             |
| 5,624,663 | A |   | 4/1997  | Deflandre et al.  |             |
| 6,093,385 | A |   | 7/2000  | Habeck et al.     |             |
| 6,159,455 | A |   | 12/2000 | Habeck et al.     |             |
| 6,387,355 | B2|   | 5/2002  | Heidenfelder et al.|            |
| 6,391,289 | B2|   | 5/2002  | Heidenfelder et al.|            |
| 6,436,373 | B1|   | 8/2002  | Habeck et al.     |             |
| 6,555,119 | B1| * | 4/2003  | Mori              | A61K 8/068  |
|           |   |   |         |                   | 424/401     |
| 2004/0115159 | A1 |  | 6/2004 | Tadlock           |             |
| 2005/0013782 | A1 |  | 1/2005 | Goppel et al.     |             |
| 2005/0287088 | A1| * | 12/2005 | Guiramand        | A61K 8/062  |
|           |   |   |         |                   | 424/59      |
| 2005/0287104 | A1| * | 12/2005 | Aubrun-Sonneville | A61K 8/0208 |
|           |   |   |         |                   | 424/70.22   |
| 2006/0233721 | A1| * | 10/2006 | Tamarkin         | A61K 8/046  |
|           |   |   |         |                   | 424/47      |
| 2007/0237798 | A1| * | 10/2007 | Apostol          | A61K 8/062  |
|           |   |   |         |                   | 424/401     |
| 2008/0153929 | A1|   | 6/2008  | Miyahara et al.  |             |
| 2008/0253986 | A1| * | 10/2008 | Mallard          | A61K 8/04   |
|           |   |   |         |                   | 424/78.37   |
| 2012/0128601 | A1|   | 5/2012  | Behler           |             |
| 2012/0321576 | A1|   | 12/2012 | Sugiyama et al.  |             |

FOREIGN PATENT DOCUMENTS

| DE | 19726184 A1 | 12/1998 |
| DE | 19746654 A1 | 2/1999  |
| DE | 19755649 A1 | 6/1999  |
| DE | 19855649 A1 | 6/2000  |
| DE | 10162844 A1 | 7/2003  |
| EP | 0669323 A1  | 8/1995  |
| EP | 0832642 A2  | 4/1998  |
| EP | 0893119 A1  | 1/1999  |
| EP | 0967200 A1  | 12/1999 |
| EP | 1008586 A1  | 6/2000  |
| EP | 1027883 A2  | 6/2000  |
| EP | 1133980 A2  | 9/2001  |
| EP | 1133981 A2  | 9/2001  |
| EP | 1300137 A2  | 4/2003  |

(Continued)

OTHER PUBLICATIONS

International Search Report dated Nov. 13, 2015.

*Primary Examiner* — Tracy Vivlemore
*Assistant Examiner* — Monica A Shin
(74) *Attorney, Agent, or Firm* — McNees Wallace & Nurick LLC

(57) ABSTRACT

The present invention relates to a sunscreen composition comprising:

a. an aqueous phase;

b. an oil phase comprising at least one cosmetically acceptable oil;

c. at least one sunscreen active; and d. up to about 5% by weight, based on the total weight of the composition, of an emulsifier system comprising;

i. at least one ionic surfactant;

ii. at least one nonionic surfactant having an HLB of greater than or equal to about 14; and iii. at least one nonionic surfactant having an HLB of less than or equal to about 10;

wherein the composition is an oil-in-water emulsion containing oil droplets having an average particle size of from about 100 to 150 nm, is alcohol-free, and appears semi-transparent to transparent upon application onto an end-user's skin.

41 Claims, No Drawings

(56) References Cited

FOREIGN PATENT DOCUMENTS

| EP | 1616552 A1 | 1/2006 |
|----|------------|--------|
| GB | 2303549 A | 2/1997 |
| WO | 2004/006878 A1 | 1/2004 |
| WO | 2005/058269 A1 | 6/2005 |
| WO | 2006/032741 A1 | 3/2006 |
| WO | 2006/034982 A1 | 4/2006 |
| WO | 2006/034985 A1 | 4/2006 |
| WO | 2006/034991 A1 | 4/2006 |
| WO | 2006/034992 A1 | 4/2006 |
| WO | 2006/035000 A1 | 4/2006 |
| WO | 2006/035007 A1 | 4/2006 |
| WO | 2012/081446 A1 | 6/2012 |
| WO | 2014105877 A1 | 7/2014 |

* cited by examiner

HIGH UV PROTECTION ALCOHOL-FREE EMULSION SYSTEM, THAT IS CLEAR ON APPLICATION

BACKGROUND OF THE INVENTION

Conventional sunscreen products generally contain ultraviolet (UV)-filter compounds and/or particulate UV-screening compounds (collectively, "sunscreen actives") that are solubilized, emulsified, or dispersed in a vehicle, which is topically applied to the skin. The sunscreen actives, typically through the aid of polymers and other ingredients included in the vehicle form a thin, protective, and water-resistant layer on the skin.

Transparent personal care and cosmetic products have become increasingly important to the consumer. Transparent products may be perceived as light, clean, fresh, and cooling. Among sunscreen products, sprays are gaining increasing consumer preference because of their convenience and ease of application.

Currently marketed transparent sunscreen sprays are typically oil-based or alcohol-based formulas. Alcohol-based formulas may contain more than 60% alcohol in order to dissolve the organic UV filters. Additionally, the high alcohol content allows for easy application and quick drying. However, there are numerous safety concerns associated with alcohol-containing formulas. Products containing alcohols require special safety measures to be taken during production, storage, and transport. In addition, alcohol-containing products are potentially flammable during use. As a result, alcohol-free products are preferred by consumers because of odor, tolerance, and safety considerations.

While oil-in-water emulsions are an alternative to alcohol- or oil-based formulas, they are typically opaque in appearance. Obtaining transparency in a classical oil-in-water emulsion is not easily achieved. One method of obtaining transparent oil-in-water emulsions requires the use of high levels of surfactant which may result in skin irritation and an unpleasant sticky feel upon application. Additionally, high levels of surfactants in sunscreen products may cause the product to be less water resistant. Since water resistance is critical to a sunscreen product's efficacy, the deleterious effect on water resistance caused by high levels of surfactants renders this solution to providing transparency unacceptable.

It is thus an object of the present invention to provide a sunscreen product that is transparent in appearance, and does not possess the above-mentioned drawbacks.

BRIEF SUMMARY OF THE INVENTION

The present invention relates to a sunscreen composition comprising:
a. an aqueous phase;
b. an oil phase comprising at least one cosmetically acceptable oil;
c. at least one sunscreen active; and
d. up to about 5% by weight, based on the total weight of the composition, of an emulsifier system comprising;
  i. at least one ionic surfactant;
  ii. at least one nonionic surfactant having an HLB of greater than or equal to about 14; and
  iii. at least one nonionic surfactant having an HLB of less than or equal to about 10:
wherein the composition is an oil-in-water emulsion containing oil droplets having an average particle size of from about 100 to 150 nm, is alcohol-free, and appears semi-transparent to transparent upon application onto an end-user's skin.

The present invention is also directed to a method of making a sunscreen composition by combining the above-disclosed ingredients, wherein the resultant composition is an oil-in-water emulsion containing oil droplets having an average particle size of from about 100 to 150 nm, is alcohol-free and semi-transparent to transparent in appearance during application onto an end-user's skin.

The present invention is also directed to a method of inhibiting UV radiation from contacting a keratinous substrate by applying the above-disclosed sunscreen composition onto a surface of the keratinous substrate.

DETAILED DESCRIPTION OF THE INVENTION

Other than in the operating examples, or where otherwise indicated, all numbers expressing quantities of ingredients and/or reaction conditions are to be understood as being modified in all instances by the term "about".

As used herein, the expression "at least one" means one or more and thus includes individual components as well as mixtures/combinations.

"Cosmetically acceptable" means compatible with any keratinous substrate. For example, "cosmetically acceptable carrier" means a carrier that is compatible with any keratinous substrate.

A "physiologically acceptable medium" means a medium which is not toxic and can be applied to the skin, lips, hair, scalp, lashes, brows, nails or any other cutaneous region of the body. The composition of the instant disclosure may especially constitute a cosmetic or dermatological composition.

The terms "semi-transparent" and "transparent" as used herein means that the emulsion contains oil droplets having an average particle size ranging from about 100 to 150 nm.

"Average particle size" as used herein is determined by dynamic light scattering using a Brookhaven Instruments OLS particle size analyzer '90 plus'.

Emulsifier System

The emulsifier system is comprised of at least one ionic surfactant, at least one nonionic surfactant having an HLB of greater than or equal to about 14, and at least one nonionic surfactant having an HLB of less than or equal to about 10.

Suitable ionic surfactants for use in the present invention include, but are not limited to:
alkali metal salts of dicetyl phosphate and of dimyristyl phosphate;
alkali metal salts of cholesterol sulphate;
alkali metal salts of cholesterol phosphate;
lipoamino acids and their salts, such as mono and disodium acylglutamates, for instance the disodium salt of N-stearoyl-L-glutamic acid sold under the trade name AMISOFT® HS 21P by the company Ajinomoto;
sodium salts of phosphatidic acid;
phospholipids;
alkylsulphonic derivatives, in particular of formula (I):

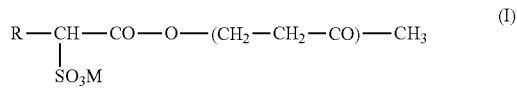

in which R represents C16-C22 alkyl radicals, in particular the C16H33 and C18H37 radicals taken as a mixture or separately, and M is an alkali metal or alkaline earth metal, such as sodium; and mixtures thereof.

Particularly preferred ionic surfactants are sodium stearoyl glutamate and disodium stearoyl glutamate.

The ionic surfactant will typically be employed in an amount of from about 0.05 to about 1.0% by weight, preferably from about 0.1 to about 0.5% by weight, and most preferably from about 0.2 to about 0.3% by weight, based on the total weight of the composition.

Suitable nonionic surfactants having an HLB greater than or equal to about 14 include, but are not limited to, polysorbate 60, polysorbate 20, polysorbate 21, polysorbate 40, polysorbate 80, and mixtures thereof.

A particularly preferred polysorbate is polysorbate 60.

The at least one nonionic surfactant having an HLB of greater than or equal to about 14 will typically be employed in an amount of from about 1.0 to 3.0% by weight, preferably from about 1.25 to 2.75% by weight, and most preferably from about 1.5 to 2.5% by weight, based on the total weight of the composition.

Suitable nonionic surfactants having an HLB of less than or equal to about 10 include, but are not limited to, polyglycerides, polysorbate 61, polysorbate 65, polysorbate 81, polysorbate 85, and mixtures thereof.

Particularly preferred nonionic surfactants having an HLB of less than or equal to about 10 include polysorbate 61 and polyglyceryl-2 laurate.

The at least one nonionic surfactant having an HLB of less than or equal to about 10 will typically be employed in an amount of from about 1 to 3% by weight, preferably from about 1.25 to 2.75% by weight, and most preferably from about 1.5 to 2.5% by weight, based on the total weight of the composition.

The emulsifier system will typically be present in the composition in an amount of up to about 5% by weight, preferably up to about 4.5% by weight, and most preferably up to about 4.25% by weight, based on the total weight of the composition.

It is imperative that the emulsifier system be employed in the above-disclosed amounts so that the oil droplets present in the composition possess the desired average particle size. Without intending to be bound by theory, it is believed that the average particle size of the oil droplets is what facilitates the composition having a semi-transparent to transparent appearance during application onto an end-user's skin.

Oil Phase

The oil phase of the present invention is comprised of at least one oil.

Suitable oils include, but are not limited to:
mineral oils, such as hexadecane, isohexadecane and liquid paraffin;
animal or plant oils formed by fatty acid esters of polyols, in particular liquid triglycerides, for example sunflower oil, corn oil, soybean oil, avocado oil, jojoba oil, marrow oil, grapeseed oil, sesame oil, hazelnut oil, fish oils, glyceryl tricaprocaprylate, purcellin oil, or liquid jojoba wax;
natural or synthetic essential oils such as, for example, eucalyptus oil, lavandin oil, lavender oil, vetivier oil, litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil;
synthetic oils such as parleam oil, polyolefins and liquid carboxylic acid esters; halogenated oils, in particular fluorocarbons, such as fluoroamines, for example perfluorotributylamine, fluorinated hydrocarbons, for example perfluoro-decahydronaphthalene, fluoroesters and fluoroethers;
volatile and non-volatile silicone oils;
polyolefins, in particular poly-α-olefins, and more particularly those of hydrogenated or nonhydrogenated polybutene type, and preferably hydrogenated or nonhydrogenated polyisobutene type;
esters of mono-, di-, tri- or tetracarboxylic acids, in particular alkyl palmitates, such as ethyl palmitate, isopropyl palmitate, 2-ethylhexyl palmitate, 2-octyldecyl palmitate; alkyl myristates, such as isopropyl myristate, butyl myristate, cetyl myristate, 2-octyldodecyl myristate; alkyl stearates, such as hexyl stearate, butyl stearate or isobutyl stearate; alkyl malates, such as dioctyl malate; alkyl laurates, such as hexyl laurate and 2-hexyldecyl laurate, isononyl isononanoate, or cetyl octanoate; and mixtures thereof.

The oil phase will typically be employed in an amount of from about 1 to 15% by weight, preferably from about 2 to 10% by weight, and more preferably from about 3% to 8% by weight, based on the total weight of the composition.

Sunscreen Actives

Suitable UV-screening agents include, but are not limited to, cinnamic derivatives; anthranilates; salicylic derivatives; dibenzoylmethane derivatives; camphor derivatives; benzophenone derivatives; β,β-diphenylacrylate derivatives; triazine derivatives; benzotriazole derivatives; benzalmalonate derivatives, especially those cited in U.S. Pat. No. 5,624,663; benzimidazole derivatives; imidazolines; bis-benzoazolyl derivatives as described in patents EP669323 and U.S. Pat. No. 2,463,264; p-aminobenzoic acid (PABA) derivatives; methylene bis(hydroxyphenylbenzotriazole) derivatives as described in applications U.S. Pat. No. 5,237,071, U.S. Pat. No. 5,166,355, GB2303549, DE19726184 and EP893119; benzoxazole derivatives as described in patent applications EP0832642, EP1027883, EP1300137 and DE10162844; screening polymers and screening silicones such as those described especially in patent application WO 93/04665; dimers derived from α-alkylstyrene such as those described in patent application DE 19855649; 4,4-diarylbutadienes such as those described in patent applications EP0967200, DE19746654, DE19755649, EP-A-1008586, EP1133980 and EP1133981, merocyanine derivatives such as those described in patent applications WO 04/006878, WO 05/058269 and WO 06/032741; and mixtures thereof.

As examples of complementary organic photoprotective agents, mention may be made of those denoted herein below under their INCI name:

Cinnamic Derivatives:
Ethylhexyl Methoxycinnamate sold in particular under the trade name "Parsol® MCX" by DSM Nutritional Products, Isopropyl Methoxycinnamate, Isoamyl Methoxycinnamate sold under the trade name "Neo Heliopan® E 1000" by Symrise, DEA Methoxycinnamate, Diisopropyl Methylcinnamate, Glyceryl Ethylhexanoate Dimethoxycinnamate.

Dibenzoylmethane Derivatives:
Butyl Methoxydibenzoylmethane sold especially under the trade name "Parsol® 1789" by DSM, Isopropyl Dibenzoylmethane.

Para-Aminobenzoic Acid Derivatives:
PABA, Ethyl PABA, Ethyl Dihydroxypropyl PABA, Ethylhexyl dimethyl PABA sold in particular under the name "Escalol™ 507" by ISP, Glyceryl PABA, PEG-25 PABA sold under the name "Uvinul® P25" by BASF.

Salicylic Derivatives:
   Homosalate sold under the name "Eusolex® HMS" by Rona/EM Industries, Ethylhexyl Salicylate sold under the name "Neo Heliopan® OS" by Symrise, Dipropylene Glycol Salicylate sold under the name Dipsal™ by Scher, TEA Salicylate sold under the name "Neo Heliopan® TS" by Symrise.

β,β-Diphenylacrylate Derivatives:
   Octocrylene sold in particular under the trade name "Uvinul® N539" by BASF, Etocrylene sold in particular under the trade name "Uvinul® N35" by BASF.

Benzophenone Derivatives:
   Benzophenone-1 sold under the trade name "Uvinul® 400" by BASF, Benzophenone-2 sold under the trade name "Uvinul® D50" by BASF, Benzophenone-3 or Oxybenzone sold under the trade name "Uvinul® M40" by BASF, Benzophenone-4 sold under the trade name "Uvinul® MS40" by BASF, Benzophenone-5, Benzophenone-6 sold under the trade name "Helisorb® 11" by Norquay, Benzophenone-8 sold under the trade name "Spectra-Sorb UV-24" by American Cyanamid, Benzophenone-9 sold under the trade name "Uvinul® DS-49" by BASF, Benzophenone-12, n-Hexyl 2-(4-diethylamino-2-hydroxybenzoyl)benzoate sold under the trade name "Uvinul® A+" or as a mixture with octyl methoxycinnamate under the trade name "Uvinul® A+B" by BASF.

Benzylidenecamphor Derivatives:
   3-Benzylidene Camphor manufactured under the name "Mexoryl™ SD" by Chimex, 4-Methylbenzylidene Camphor sold under the name "Eusolex® 6300" by Merck, Benzylidene Camphor Sulfonic Acid manufactured under the name "Mexoryl™ SL" by Chimex, Camphor Benzalkonium Methosulfate manufactured under the name "Mexoryl™ SO" by Chimex, Terephthalylidene Dicamphor Sulfonic Acid manufactured under the name "Mexoryl™ SX" by Chimex, Polyacrylamidomethyl Benzylidene Camphor manufactured under the name "Mexoryl™ SW" by Chimex.

Phenylbenzimidazole Derivatives:
   Phenylbenzimidazole Sulfonic Acid sold in particular under the trade name "Eusolex® 232" by Merck, Disodium Phenyl Dibenzimidazole Tetrasulfonate sold under the trade name "Neo Heliopan® AP" by Symrise.

Phenylbenzotriazole Derivatives:
   Drometrizole Trisiloxane sold under the name "Silatrizole" by Rhodia Chimie, Methylene bis-Benzotriazolyl Tetramethylbutyl-phenol sold in solid form under the trade name "MIXXIM BB/100" by Fairmount Chemical, or in micronized form as an aqueous dispersion under the trade name "Tinosorb M" by Ciba Specialty Chemicals.

Triazine Derivatives:
   bis-Ethylhexyloxyphenol Methoxyphenyl Triazine sold under the trade name "Tinosorb® S" by BASF, Ethylhexyl Triazone sold in particular under the trade name "Uvinul® T150" by BASF, Diethylhexyl Butamido Triazone sold under the trade name "Uvasorb® HEB" by Sigma 3V, 2,4,6-tris(dineopentyl 4'-aminobenzalmalonate)s-triazine, 2,4,6-tris(diisobutyl 4'-aminobenzalmalonate)s-triazine, 2,4-bis(dineopentyl 4'-aminobenzalmalonate)-6-(n-butyl 4'-aminobenzoate)-s-triazine, symmetrical triazine screening agents described in U.S. Pat. No. 6,225,467, patent application WO 2004/085412 (see compounds 6 and 9) or the document "Symmetrical Triazine Derivatives" IP.COM Journal, IP.COM Inc., West Henrietta, N.Y., US (20 Sep. 2004), especially 2,4,6-tris(biphenyl)-1,3,5-triazines (in particular 2,4,6-tris(biphenyl-4-yl)-1,3,5-triazine and 2,4,6-tris(terphenyl)-1,3,5-triazine, which is included in patent applications WO 06/035000, WO 06/034982, WO 06/034991, WO 06/035007, WO 2006/034992 and WO 2006/034985).

Anthranilic Derivatives:
   Menthyl Anthranilate sold under the trade name "Neo Heliopan® MA" by Symrise.

Imidazoline Derivatives:
   Ethylhexyl Dimethoxybenzylidene Dioxoimidazoline Propionate.

Benzalmalonate Derivatives:
   Polyorganosiloxane containing benzalmalonate functions, for instance Polysilicone-15, sold under the trade name "Parsol® SLX" by DSM Nutritional Products.

4,4-Diarylbutadiene Derivatives:
   1,1-dicarboxy(2,2'-dimethylpropyl)-4,4-diphenylbutadiene.

Benzoxazole Derivatives:
   2,4-bis[5-(1-dimethylpropyl)benzoxazol-2-yl-(4-phenyl)imino]-6-(2-ethylhexyl)imino-1,3,5-triazine sold under the name Uvasorb® K2A by Sigma 3V, and mixtures thereof.

Preferred Organic Screening Agents are Chosen from:
   Ethylhexyl Methoxycinnamate, Ethylhexyl Salicylate, Homosalate, Butyl Methoxydibenzoylmethane. Octocrylene, Phenylbenzimidazole Sulfonic Acid, Benzophenone-3, Benzophenone-4, Benzophenone-5, n-Hexyl 2-(4-diethylamino-2-hydroxybenzoyl)benzoate, 4-Methylbenzylidene Camphor, Terephthalylidene Dicamphor Sulfonic Acid, Disodium Phenyl Dibenzimidazole Tetrasulfonate, Methylene Bis-Benzotriazolyl Tetramethylbutylphenol, Bis-Ethylhexyloxyphenol Methoxyphenyl Triazine, Ethylhexyl triazone, Diethylhexyl Butamido Triazone, 2,4,6-Tris(dineopentyl 4'-aminobenzalmalonate)-s-triazine, 2,4,6-Tris(diisobutyl 4-aminobenzalmalonate)-s-triazine, 2,4-Bis(dineopentyl 4-aminobenzalmalonate)-6-(n-butyl 4'-aminobenzoate)-s-triazine, 2,4,6-Tris(biphenyl-4-yl)-1,3,5-triazine, 2,4,6-Tris(terphenyl)-1,3,5-triazine, Drometrizole Trisiloxane, Polysilicone-15, 1,1-dicarboxy(2,2'-dimethylpropyl)-4,4'-diphenylbutadiene, 2,4-bis[5-1(dimethylpropyl)benzoxazol-2-yl-(4-phenyl)imino]-6-(2-ethylhexyl)imino-1,3,5-triazine, and mixtures thereof.

The sunscreen actives according to the invention are typically present in the composition in an amount ranging from about 25 to 40% by weight, preferably from about 25% to 35% by weight, and most preferably from about 25 to 30% by weight, based on the total active weight of the composition, if a composition having an SPF of from about 50 to 100 is desired.

On the other hand, if a composition having an SPF of from about 15 to about 50 is desired, the sunscreen actives will be employed in an amount ranging from about 10 to 25% by weight, preferably from about 12% to 25% by weight, and most preferably from about 15 to 25% by weight, based on the total active weight of the composition.

Optional Solvents
   The composition may optionally comprise at least one solvent. The at least one solvent may be chosen from:
   glycols, such as glycerol, propylene glycol, 1,3 butylene glycol, caprylyl glycol, dipropylene glycol or polyethylene glycols comprising from 4 to 16 ethylene oxide units, and preferably from 8 to 12;
   glycol ethers, such as phenoxyethanol, di(ethylene glycol) ethyl ether, also known as ethoxy diglycol, 2-(2-ethoxyethoxy)ethanol, diglycolmonoethyl ether, ethyl diethylene glycol, ethylene diglycol monoethyl ether, di(ethylene glycol) ethyl ether, methoxyisopropanol, PPG-2 methyl ether, PPG-3 methyl ether, propylene glycol butyl ether, PPG-2 butyl ether, phenoxyisopropanol, butoxyethanol, butoxydiglycol, methoxydiglycol, PPG-3 butyl ether, PPG-2 propyl ether, propylene glycol propyl ether, or dipropylene glycol dimethyl ether; and mixtures thereof.

The at least one solvent may be employed in an amount of from about 0.25 to 15% by weight, preferably from about 1 to 10% by weight, and more preferably from about 2 to 8% by weight, based on the total weight of the composition.

The composition of the invention may also contain adjuvants, and in particular water-soluble or liposoluble active agents having a cosmetic or dermatological activity. By way of examples of active agents, mention may be made of vitamins and their derivatives, such as vitamin E and its esters, for instance vitamin E acetate, vitamin C and its esters, B vitamins, vitamin A alcohol or retinol and its esters, such as vitamin A palmitate, vitamin A acid or retinoic acid and its derivatives, provitamins such as panthenol and niacinamide, ergocalciferol, antioxidants, essential oils, humectants, sunscreens, moisturizers, proteins, ceramides and pseudoceramides, and DHEA and its derivatives and biological precursors. As adjuvants, mention may also be made of sequestering agents, preserving agents, fillers, softeners, dyestuffs (pigments or dyes) and fragrances.

The amounts of these various adjuvants are those conventionally used in the field under consideration, and are, for example, from 0.01% to 20% of the total weight of the composition. These adjuvants and the concentrations thereof should be such that they do not modify the property desired for the composition of the invention.

EXAMPLES

TABLE 1

| Ingredients | Inventive Examples | | | | |
|---|---|---|---|---|---|
|  | Ex. 1 | Ex. 2 | Ex. 3 | Ex. 4 | Ex. 5 |
| Phase A |  |  |  |  |  |
| SUNSCREEN ACTIVES | 20.0 | 20.0 | 20.0 | 20.0 | 20.0 |
| ISOHEXADECANE | 5.0 | 5.0 | 5.0 | 5.0 | 5.0 |
| POLYSORBATE 61 | 2.5 | 3.0 | 2.5 | 2.5 | — |
| POLYSORBATE 60 | 1.5 | 1.0 | 1.5 | 1.5 | 3.0 |
| POLYGLYCERYL-2 LAURATE | — | — | — | — | 1.0 |
| DISODIUM STEAROYL GLUTAMATE | 0.25 | 0.25 | 0.25 | — | 0.25 |
| SODIUM STEAROYL GLUTAMATE | — | — | — | 0.25 | — |
| CAPRYLYL GLYCOL | 1.0 | 1.0 | 1.0 | 1.0 | 1.0 |
| PHENOXYETHANOL | 1.0 | 1.0 | 1.0 | 1.0 | 1.0 |
| Phase A2 |  |  |  |  |  |
| ALCOHOL DENAT. | — | — | 5.0 | — | 5.0 |
| Phase B |  |  |  |  |  |
| PEG-8 | 5.0 | 5.0 | 5.0 | 5.0 | 5.0 |
| DISODIUM EDTA | 0.10 | 0.10 | 0.10 | 0.01 | 0.01 |
| WATER | 38.65 | 38.65 | 33.65 | 38.65 | 33.65 |
| Phase C |  |  |  |  |  |
| WATER | 25.0 | 25.0 | 25.0 | 25.0 | 25.0 |
| Average Particle Size of Oil Droplets (nm) | 126 | 126 | 139 | 132 | 119 |
| Stable Emulsion | Yes | Yes | Yes | Yes | Yes |

TABLE 2

| Ingredients | Comparative Examples | |
|---|---|---|
|  | Ex. 6 | Ex. 7 |
| Phase A |  |  |
| SUNSCREEN ACTIVES | 20.0 | 20.0 |
| ISOHEXADECANE | 5.0 | 5.0 |
| POLYSORBATE 61 | 3.5 | 0.5 |
| POLYSORBATE 60 | 0.5 | 3.5 |
| DISODIUM STEAROYL GLUTAMATE | 0.25 | 0.25 |
| CAPRYLYL GLYCOL | 1.0 | 1.0 |
| PHENOXYETHANOL | 1.0 | 1.0 |
| Phase B |  |  |
| PEG-8 | 5.0 | 5.0 |
| DISODIUM EDTA | 0.10 | 0.10 |
| WATER | 38.65 | 38.65 |
| Phase C |  |  |
| WATER | 25.0 | 25.0 |
| Average Particle Size of Oil Droplets (nm) measured at time = 0 | 153 | 147 |
| Stable Emulsion | No | No |

In making each of the examples in Tables 1 and 2, the following procedure was used. Phases A and B were heated to 50° C. Phase B was added to phase A and homogenized with a high speed mixer for 15 minutes at 4500 rpm. The resulting emulsion was passed two times through a high pressure homogenizer at 700 bar. Phase C was added to the emulsion and mixed with an overhead blade for 10 minutes.

A Brookhaven Instruments DLS particle size analyzer '90 plus' was then used to measure the effective particle size of the emulsions. The samples were diluted with deionized water and measurements run for 2 minutes, at ambient temperature. The "effective diameter" was reported.

Examples 6 and 7 demonstrate the criticality of the emulsifier system. When the emulsifier system fails to correspond to the inventive emulsifier system, the composition yields an unstable emulsion which is neither semitransparent nor transparent.

What is claimed is:
1. A process for making a sunscreen composition comprising:
   a) Providing an aqueous phase;
   b) Providing an oil phase comprising at least one cosmetically acceptable oil;
   c) Providing at least one sunscreen active;
   d) Providing up to about 5% by weight, based on the total weight of the composition, of an emulsifier system comprising;
      i) at least one ionic surfactant;
      ii) from about 1 to about 3% by weight, based on the weight of the composition, of at least one nonionic surfactant having an HLB of greater than or equal to about 14; and
      iii) from about 1 to 3% by weight, based on the weight of the composition, of at least one nonionic surfactant having an HLB of less than or equal to about 10; and
   e) Combining a) to d) to form the sunscreen composition, the sunscreen composition having from about 12% to about 25% by weight sun screen active or from about 25 to about 40% by weight sun screen active, based on the total weight of the composition,
   wherein the composition is an oil-in-water emulsion containing oil droplets having an average particle size of from about 100 to 150 nm, is denatured alcohol-free, appears semi-transparent to transparent upon application onto an end-user's skin, and is stable.

2. The process of claim 1 wherein b) is employed in an amount of from about 1 to 15% by weight, based on the weight of the composition.

3. The process of claim 1 wherein b) is employed in an amount of from about 2 to 10% by weight, based on the weight of the composition.

4. The process of claim 1 wherein d) is employed in an amount of up to about 4.5% by weight, based on the weight of the composition.

5. The process of claim 1 wherein d) is employed in an amount of up to about 4.25% by weight, based on the weight of the composition.

6. The process of claim 1 wherein d) i) is employed in an amount of from about 0.05 to 1% by weight, based on the weight of the composition.

7. The process of claim 1 wherein d) i) is employed in an amount of from about 0.1 to 0.5% by weight, based on the weight of the composition.

8. The process of claim 1 wherein d) ii) is employed in an amount of from about 1.25 to 2.75% by weight, based on the weight of the composition.

9. The process of claim 1 wherein d) iii) is employed in an amount of from about 1.25 to 2.75% by weight, based on the weight of the composition.

10. The process of claim 1 further comprising providing a solvent in an amount of from about 0.25 to 15% by weight, based on the weight of the composition.

11. The process of claim 10 wherein the solvent is employed in an amount of from about 1 to 10% by weight, based on the weight of the composition.

12. A process for making a sunscreen composition comprising:
   a) Providing an aqueous phase;
   b) Providing an oil phase comprising from about 3 to 8% by weight of at least one cosmetically acceptable oil;
   c) Providing at least one sunscreen active;
   d) Providing up to about 4.25% by weight of an emulsifier system comprising;
      i) From about 0.2 to 0.3% by weight of at least one ionic surfactant;
      ii) From about 1.5 to 2.5% by weight of at least one nonionic surfactant having an HLB of greater than or equal to about 14; and
      iii) From about 1.5 to 2.5% by weight of at least one nonionic surfactant having an HLB of less than or equal to about 10, all weights being based on the total weight of the composition; and
   e) Combining a) to d) to form the sunscreen composition, the sunscreen composition having from about 12% to about 25% by weight sun screen active or from about 25 to about 40% by weight sun screen active, based on the total weight of the composition,
   wherein the composition is an oil-in-water emulsion containing oil droplets having an average particle size of from about 100 to 150 nm, is denatured alcohol-free, appears semi-transparent to transparent upon application onto an end-user's skin and is stable.

13. A composition comprising:
   a) an aqueous phase;
   b) an oil phase comprising at least one cosmetically acceptable oil;
   c) at least one sunscreen active; and
   d) up to about 5% by weight, based on the total weight of the composition, of an emulsifier system comprising;
      i) at least one ionic surfactant;
      ii) from about 1 to about 3% by weight, based on the weight of the composition, of at least one nonionic surfactant having an HLB of greater than or equal to about 14; and
      iii) from about 1 to 3% by weight, based on the weight of the composition, of at least one nonionic surfactant having an HLB of less than or equal to about 10; and
   wherein the composition is an oil-in-water emulsion containing oil droplets having an average particle size of from about 100 to 150 nm, is denatured alcohol-free, appears semi-transparent to transparent upon application onto an end-user's skin and is stable.

14. The composition of claim 13 wherein b) is employed in an amount of from about 1 to 15% by weight, based on the weight of the composition.

15. The composition of claim 13 wherein b) is employed in an amount of from about 2 to 10% by weight, based on the weight of the composition.

16. The composition of claim 13 wherein d) is employed in an amount of up to about 4.5% by weight, based on the weight of the composition.

17. The composition of claim 13 wherein d) is employed in an amount of up to about 4.25% by weight, based on the weight of the composition.

18. The composition of claim 13 wherein d) i) is employed in an amount of from about 0.05 to 1% by weight, based on the weight of the composition.

19. The composition of claim 13 wherein d) i) is employed in an amount of from about 0.1 to 0.5% by weight, based on the weight of the composition.

20. The composition of claim 13 wherein d) ii) is employed in an amount of from about 1.25 to 2.75% by weight, based on the weight of the composition.

21. The composition of claim 13 wherein d) iii) is employed in an amount of from about 1.25 to 2.75% by weight, based on the weight of the composition.

22. The composition of claim 13 further comprising providing a solvent in an amount of from about 0.25 to 15% by weight, based on the weight of the composition.

23. The composition of claim 22 wherein the solvent is employed in an amount of from about 1 to 10% by weight, based on the weight of the composition.

24. A sunscreen composition comprising:
   a) an aqueous phase;
   b) an oil phase comprising from about 3 to 8% by weight of at least one cosmetically acceptable oil;
   c) at least one sunscreen active; and
   d) up to about 4.25% by weight of an emulsifier system comprising;
      i) From about 0.2 to 0.3% by weight of at least one ionic surfactant;
      ii) From about 1.5 to 2.5% by weight of at least one nonionic surfactant having an HLB of greater than or equal to about 14; and
      iii) From about 1.5 to 2.5% by weight of at least one nonionic surfactant having an HLB of less than or equal to about 10, all weights being based on the total weight of the composition;
   wherein the composition is an oil-in-water emulsion containing oil droplets having an average particle size of from about 100 to 150 nm, is denatured alcohol-free, appears semi-transparent to transparent upon application onto an end-user's skin and is stable.

25. A process for inhibiting UV rays from contacting a keratinous substrate comprising applying the composition of claim 13 onto a surface of the keratinous substrate.

26. The process of claim 1 wherein the ionic surfactant is selected from the group consisting of alkali metal salts of dicetyl phosphate and of dimyristyl phosphate; alkali metal salts of cholesterol sulphate; alkali metal salts of cholesterol phosphate; lipoamino acids and their salts; sodium salts of phosphatidic acid; phospholipids; alkylsulphonic derivatives; and mixtures thereof.

27. The process of claim 26 wherein the lipoamino acids and their salts are selected from the group of sodium stearoyl glutamate and disodium stearoyl glutamate.

28. The process of claim 1 wherein the nonionic surfactant having an HLB of greater than or equal to about 14 is selected from the group consisting of polysorbate 60, polysorbate 20, polysorbate 21, polysorbate 40, polysorbate 80, and mixtures thereof.

29. The process of claim 1 wherein the nonionic surfactant having an HLB of less than or equal to about 10 is selected from the group consisting of polyglycerides, polysorbate 61, polysorbate 65, polysorbate 81, polysorbate 85, and mixtures thereof.

30. The composition of claim 13 wherein the ionic surfactant is selected from the group consisting of alkali metal salts of dicetyl phosphate and of dimyristyl phosphate; alkali metal salts of cholesterol sulphate; alkali metal salts of cholesterol phosphate; lipoamino acids and their salts; sodium salts of phosphatidic acid; phospholipids; alkylsulphonic derivatives; and mixtures thereof.

31. The composition of claim 30 wherein the lipoamino acids and their salts are selected from the group of sodium stearoyl glutamate and disodium stearoyl glutamate.

32. The composition of claim 13 wherein the nonionic surfactant having an HLB of greater than or equal to about 14 is selected from the group consisting of polysorbate 60, polysorbate 20, polysorbate 21, polysorbate 40, polysorbate 80, and mixtures thereof.

33. The composition of claim 13 wherein the nonionic surfactant having an HLB of less than or equal to about 10 is selected from the group consisting of polyglycerides, polysorbate 61, polysorbate 65, polysorbate 81, polysorbate 85, and mixtures thereof.

34. The sunscreen composition of claim 24 wherein the ionic surfactant is selected from the group consisting of alkali metal salts of dicetyl phosphate and of dimyristyl phosphate; alkali metal salts of cholesterol sulphate; alkali metal salts of cholesterol phosphate; lipoamino acids and their salts; sodium salts of phosphatidic acid; phospholipids; alkylsulphonic derivatives; and mixtures thereof.

35. The sunscreen composition of claim 34 wherein the lipoamino acids and their salts are selected from the group of sodium stearoyl glutamate and disodium stearoyl glutamate.

36. The sunscreen composition of claim 24 wherein the nonionic surfactant having an HLB of greater than or equal to about 14 is selected from the group consisting of polysorbate 60, polysorbate 20, polysorbate 21, polysorbate 40, polysorbate 80, and mixtures thereof.

37. The sunscreen composition of claim 24 wherein the nonionic surfactant having an HLB of less than or equal to about 10 is selected from the group consisting of polyglycerides, polysorbate 61, polysorbate 65, polysorbate 81, polysorbate 85, and mixtures thereof.

38. The composition of claim 13, wherein the composition has an SPF of 15 to 50.

39. The composition of claim 13, wherein the composition has an SPF of 50 to 100.

40. The composition of claim 24, wherein the sunscreen composition has an SPF of 15 to 50.

41. The composition of claim 24, wherein the sunscreen composition has an SPF of 50 to 100.

* * * * *